United States Patent
Castell et al.

(10) Patent No.: US 7,052,474 B2
(45) Date of Patent: May 30, 2006

(54) PHARYNGOESOPHAGEAL MONITORING SYSTEMS

(75) Inventors: Donald O. Castell, Charleston, SC (US); Jiri Kratochvil, Highlands Ranch, CO (US)

(73) Assignee: Sandhill Scientific, Inc., Highlands Ranch, CO (US)

( * ) Notice: Subject to any disclaimer, the term of this patent is extended or adjusted under 35 U.S.C. 154(b) by 13 days.

(21) Appl. No.: 09/970,443

(22) Filed: Oct. 2, 2001

(65) Prior Publication Data
US 2003/0028088 A1 Feb. 6, 2003

Related U.S. Application Data

(60) Provisional application No. 60/237,224, filed on Oct. 2, 2000.

(51) Int. Cl.
*A61B 5/00* (2006.01)
(52) U.S. Cl. .................................. 600/593; 600/587
(58) Field of Classification Search ............... 600/597, 600/587, 593, 486
See application file for complete search history.

(56) References Cited

U.S. PATENT DOCUMENTS

| | | | | |
|---|---|---|---|---|
| 4,073,287 A | | 2/1978 | Bradley et al. ............. 128/2 R |
| 4,245,645 A | | 1/1981 | Arseneault et al. ......... 128/642 |
| 4,450,527 A | | 5/1984 | Sramek ...................... 364/415 |
| 4,632,119 A | * | 12/1986 | Reichstein ................. 600/350 |
| 4,681,116 A | | 7/1987 | Settler ........................ 128/635 |
| 4,706,688 A | | 11/1987 | Don Michael et al. ..... 128/785 |
| 4,836,214 A | | 6/1989 | Sramek ...................... 128/693 |
| 4,981,470 A | | 1/1991 | Bombeck, IV ............. 128/635 |
| 5,048,532 A | * | 9/1991 | Hickey ....................... 600/488 |
| 5,117,827 A | * | 6/1992 | Stuebe et al. ............... 600/350 |
| 5,263,485 A | * | 11/1993 | Hickey ....................... 600/486 |
| 5,477,854 A | * | 12/1995 | Essen-Moller ............... 60/350 |
| 5,505,714 A | * | 4/1996 | Dassa et al. ................ 604/534 |
| 6,238,349 B1 | * | 5/2001 | Hickey ....................... 600/486 |

OTHER PUBLICATIONS

Shaker, R.; Milbrath, M.; Ren, J.; Toohill, R., Hogan, W.; Li, Q.; Hofmann, C.; "Esophagopharyngeal Distribution of Refluxed Gastric Acid in Patients With Reflux Laryngitis", Gastroenterology, vol. 109, No. 5., pp. 1575-1582, American Gastroenterology Association, 1995.

* cited by examiner

*Primary Examiner*—Robert L. Nasser
(74) *Attorney, Agent, or Firm*—Cochran Freund & Young LLC; James R. Young (57) ABSTRACT

Pharyngoesophageal monitoring systems are provided that monitor the environment of the pharynx and esophagus, and in some embodiments, detect and monitor refluxate, and may further record other physical episode data. The system may be provided, in some embodiments, as a bifurcated, adjustable, multiple internal reference probe, and methods thereof, to detect acid reflux and to monitor pH levels of acid reflux episodes simultaneously at multiple locations within the pharyngoesophageal passage. Some embodiments provide a recorder and one or a plurality of sensor arrangements, the recorder being responsive to the sensors and capable of correlation of signals generated by the sensor arrangements.

52 Claims, 7 Drawing Sheets

PHARYNGOESOPHAGEAL MONITORING SYSTEMS

This application claims the benefit of U.S. Provisional Application Ser. No. 60/237,224, filed Oct. 2, 2000, hereby incorporated by reference.

BACKGROUND OF THE INVENTION

1. Field of the Invention

The present invention relates generally to a probe for monitoring reflux of hydrochloric acid from the stomach into the esophagus, a condition known as gastroesophageal reflux disease. More particularly, the present invention is directed to a bifurcated, adjustable, multiple, internal reference probe for detecting acid reflux and monitoring pH levels of acid reflux episodes simultaneously at multiple locations within the pharyngoesophageal passage.

2. Description of the Related Art

Gastroesophageal reflux disease (GERD), often referred to as "reflux esophagitis", is a prevalent and ongoing problem for a significant number of people within the pediatric and adult populations of the United States and other countries, and a variety of otolaryngological abnormalities have been attributed to contact of gastroesophageal refluxate with respective structures of the aerodigestive tract. GERD is a condition in which stomach acids surge upward or reflux from the stomach into the esophagus. These acids may cause serious problems, including harsh burning sensations in the throat, chest, and neck, regurgitation, inhalation of refluxed material leading to aspiration pneumonia, swallowing difficulties, i.e., dysphagia, ulcerations of the esophageal lining, and esophageal cancer. GERD is generally caused by failure of a thickened area in the muscular wall (sphincter) of the lower esophagus that acts as a one-way valve between the stomach and esophagus, i.e., the GE junction, to properly close after swallowed liquid and solids are passed into the stomach. This valve is a high pressure zone of the esophagus (e.g., between 15 and 30 mm Hg pressure) called the lower esophageal sphincter (LES). The failure or ineffectiveness of the LES may be caused by a number of physical problems, such as by decreased resting tone in the ring-like, smooth-muscle layer of the LES, or by a hiatal hernia, which is an opening in the diaphragm, i.e., the hiatus, that is larger than necessary for the esophagus to pass into the abdominal cavity. A common cause of GERD is inappropriate muscular relaxation of a person's LES, even though the LES may have a normal resting pressure.

A second sphincter, called the upper esophageal sphincter (UES), is located approximately 25 cm above the LES and separates the esophagus from the pharynx. A primary function of the UES in the human body is to prevent the passage of inadvertently swallowed objects, such as fish bones, into the esophagus, although it is also implicated in controlling effects of gastroesophageal reflux. For example, gastroesophageal refluxate that gets past the UES and into the pharynx above the UES has been associated with vocal cord contact ulcer and a variety of other otolaryngological systems and disorders ranging from chronic hoarseness and laryngitis to laryngospasm, and otitis media have been attributed to contact of gastroesophageal refluxate with respective structures of the aerodigestive tract, such as subglottal strictures, and a variety of other laryngeal and head and neck abnormalities. See, e.g., R. Shaker et al., "Esophageal Distribution of Refluxed Gastric Acid in Patients with Reflux Laryngitis," Gastroenology, Vol. 109, pages 1575–82 (1995), hereby incorporated by reference.

In order to determine a proper course of treatment for a patient suffering from such abnormalities, it is helpful to know whether GERD may be an underlying cause and should be a target in the treatment. If the person has GERD, it is desirable to be able to accurately monitor gastric acid reflux episodes to determine their severity, frequency, and also whether they coincide with other events, such as eating meals, sleeping, or belching. Devices for sensing pH levels in the esophagus may include one or multiple pH sensors, such as antimony (Sb) billets, and conductive wires enclosed in a protective housing, such as a flexible plastic tube, that can be inserted into the patient's esophagus and connected to a recorder or logger outside the patient's body, where the recorder receives and records voltages from the antimony sensor(s) that are indicative of changes in pH levels, i.e., acidity, over time. The sensor(s) in the tube are generally inserted into a patient intranasally, fed downwardly through the pharynx, and into the patient's esophageal passage until the sensor(s) reaches the location(s) where it is desired to acquire the pH readings. Such multiple antimony pH sensors in a tube for insertion into the esophagus and ambulatory pH records for monitoring and recording gastroesophageal refluxate are commercially available, such as the ComforTECH (trademark) pH catheters and Biostar (trademark) recorders made by Sandhill Scientific, Highlands Ranch, Colo., USA. Other sources may include Del Mar Avionics of Ervin, Calif., and Synectics Medical, Inc., Irving, Tex.

However, for monitoring of gastroesophageal retluxate in patient-specific diagnostics of such otolaryngological symptoms and disorders as those described above, as well as in group studies of gastroesophageal refluxate effects, it is often desirable to have the antimony sensors positioned in specific locations in the pharynx (above the UES), proximal esophagus (below the UES), and distal esophagus (above the LES). For example, a physician might want a first antimony sensor positioned in the distal esophagus a specific distance, such as about 5 cm above the LES to detect and monitor when refluxate gets through the LES and into the distal esophagus, how acidic it is, and how long it remains in the distal esophagus before it clears. At the same time, the physician may want to also position a second antimony pH sensor a specific distance, such as about 3 cm, below the UES to detect and monitor when such refluxate gets all the way up to the proximal esophagus just under the UES, how acidic it is, and how long it remains in the proximal esophagus before it clears. It may be useful to also position even a third antimony pH sensor a specific distance, such as about 2 cm, above the UES to detect and monitor whether refluxate gets through the UES and into the pharynx, and, if so, how acidic it is, and how long it remains in the pharynx before it clears. However, the length of the esophagus, i.e., the distance between the LBS and the UES, varies from person to person, so conventional probes or catheters with multiple pH sensors do not meet this requirement. Therefore, a need may have previously existed and may have been identified by those in the relevant fields as a deficiency in heretofore previous systems. A previous attempt described in the Shaker et al. article cited above may have addressed the issue by using two separate probes with two separate recorders simultaneously, a single-site pH probe and recorder made by Del Mar Avionics, Ervin, Calif., and a dual-site pH probe and recorder made by Synectics Medical, Inc., Irving, Tex., and then correlating the data from both probes.

The described method of Shaker et al., however, may be unsatisfactory for clinical use by doctors, nurses, and patients who do not have the time, training, or patience to calibrate, install, monitor, and correlate data from two separate probes and recorders.

SUMMARY OF THE INVENTION

Accordingly, it is an object of this invention to provide a system that adequately monitors the environment of the pharynx and esophagus, and in some embodiments, detects and monitors refluxate. A goal, therefore, is to provide an apparatus having one or multiple sensors, and in some embodiments pH sensors, and which is insertable into a person's pharynx and esophagus.

An object of the present invention is also to detect, monitor and record gastroesophageal refluxate at specific desired locations. A further goal is to detect, monitor and record wherein distance between at least some of the pH sensors is adjustable, and in preferred embodiments, to accommodate positioning the pH sensors in different positions, respectively, and, in some embodiments, in relation to the person's LES, UES, and portions of the pharynx and esophagus, as well as to accommodate variations in distances between the LES's and UES's of different individuals. Another goal of this invention is also to provide an apparatus comprising a plurality of pH sensors that are adjustable in a catheter.

Another object of the present invention is to simplify calibration and acquisition, recording and display of data regarding the pharynx and esophagus conditions and reflux data, such as pH, time, and external physical episode data, in a coherent manner.

Additional objects, advantages, and novel features of the invention are set forth in part in the description that follows and will become apparent to those skilled in the art upon examination of the following description and figures or may be learned by practicing the invention. Further, the objects and the advantages may be realized and attained by means of the instrumentalities, methods, and processes, and in combinations particularly pointed out in the appended claims.

To achieve the foregoing and other objects and in accordance with the purposes of the present invention, as embodied and broadly described herein, the present invention may provide a system having a recorder, and in some embodiments, a recorder responsive to each of the pH probes. The present invention may, therefore, reduce instances of inaccurate readings, some inaccuracies occurring when a patient is required to manually track episodes of heartburn or pain, or events such as meals and recumbent periods, or when a monitoring system is used which contains segregated electrical circuits for tracking such information. In addition to the features briefly discussed in the foregoing summary, numerous features, along with their advantages, of the present invention will be apparent to those skilled in the art upon consideration of the following detailed description.

BRIEF DESCRIPTION OF THE DRAWINGS

The accompanying drawings, which are incorporated in and form a part of the specification, illustrate preferred embodiments of the present invention, and, together with the descriptions, serve to explain principles of the invention.

DETAILED DESCRIPTION OF THE PREFERRED EMBODIMENTS

Figure 1:
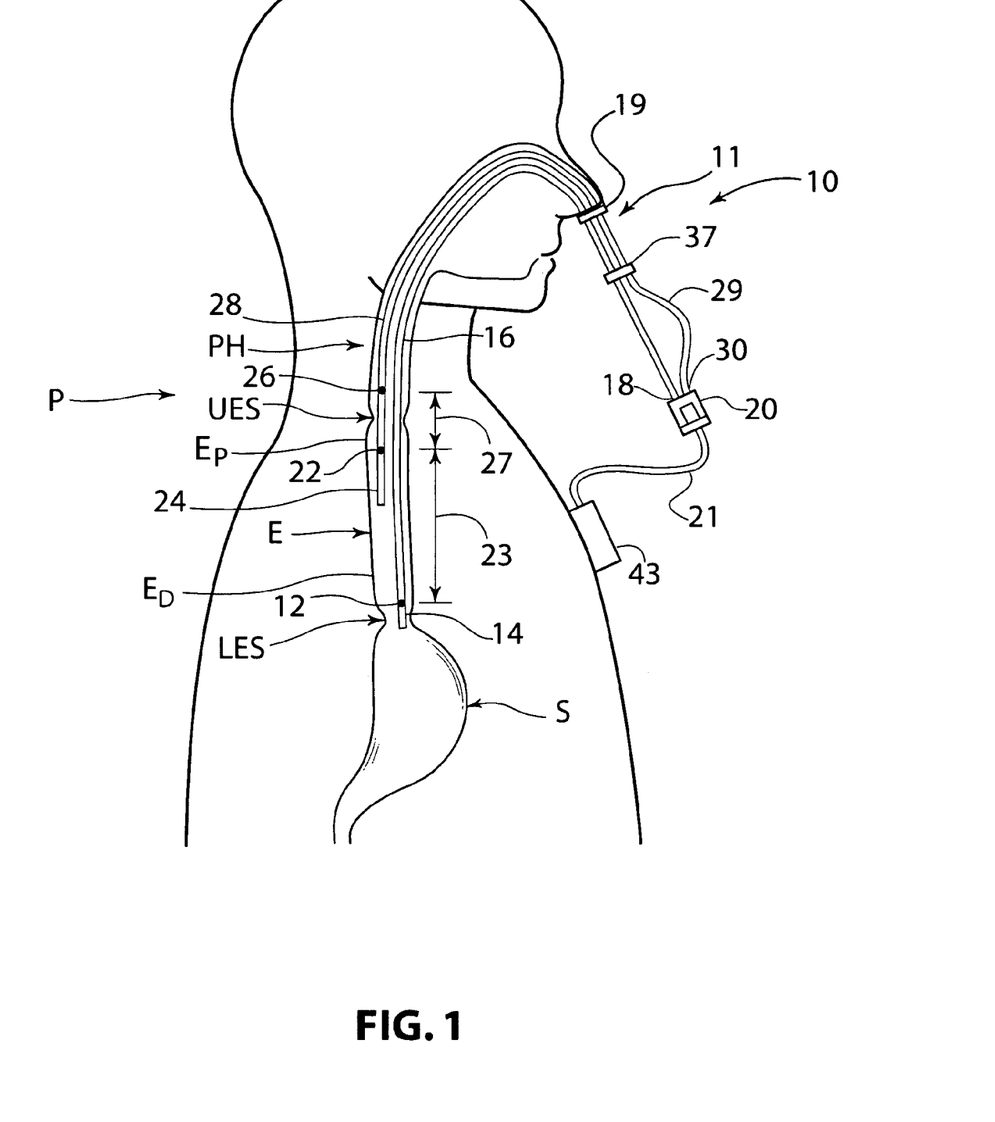
FIG. 1 is a diagrammatic front elevation view of a monitoring system in accordance with one embodiment of the present invention shown positioned in a patient's pharynx and esophagus in a manner that represents its use during monitoring.
Figure 2:
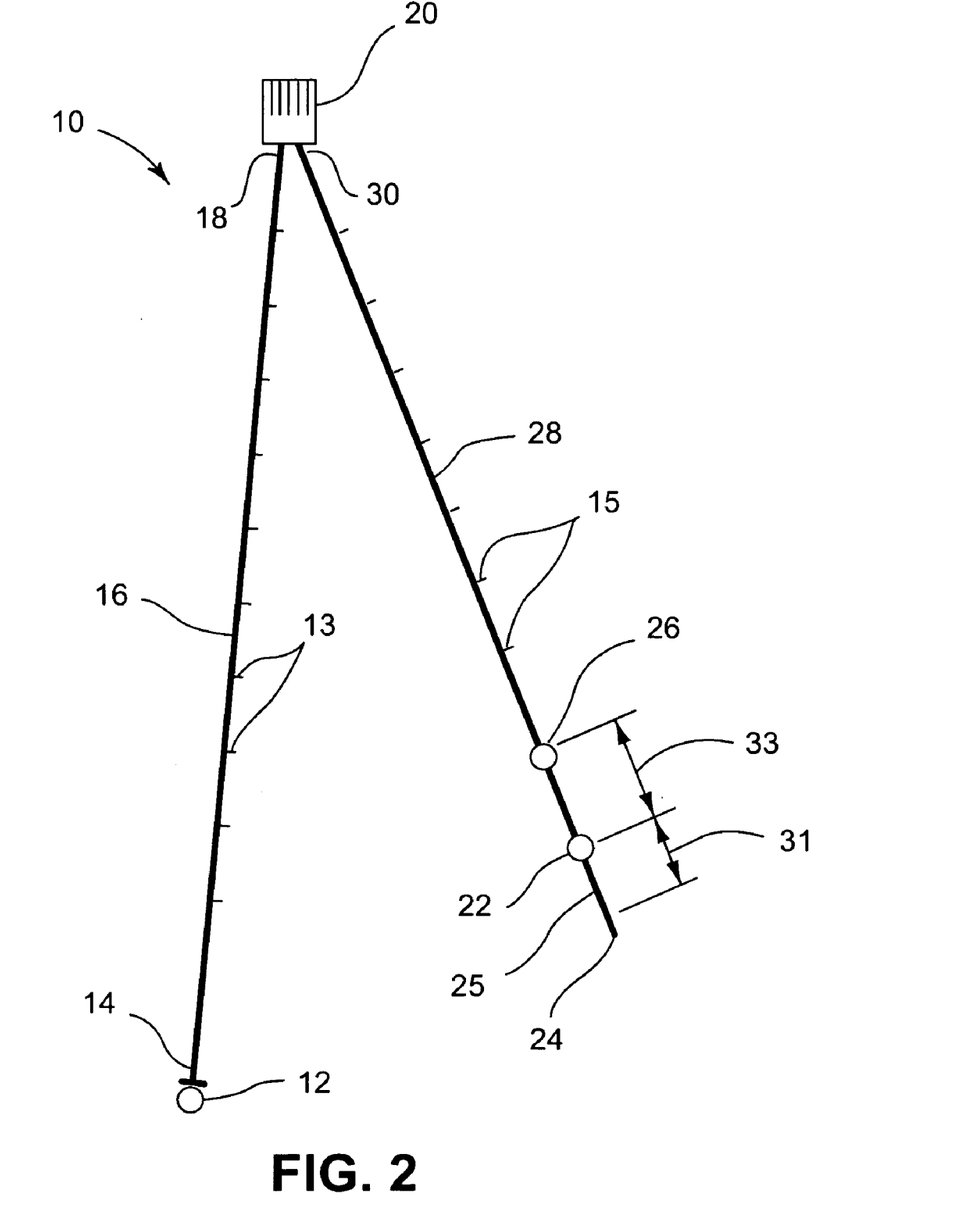
FIG. 2 is a diagrammatic view of one embodiment of the present invention having three sensors.
Figure 3:
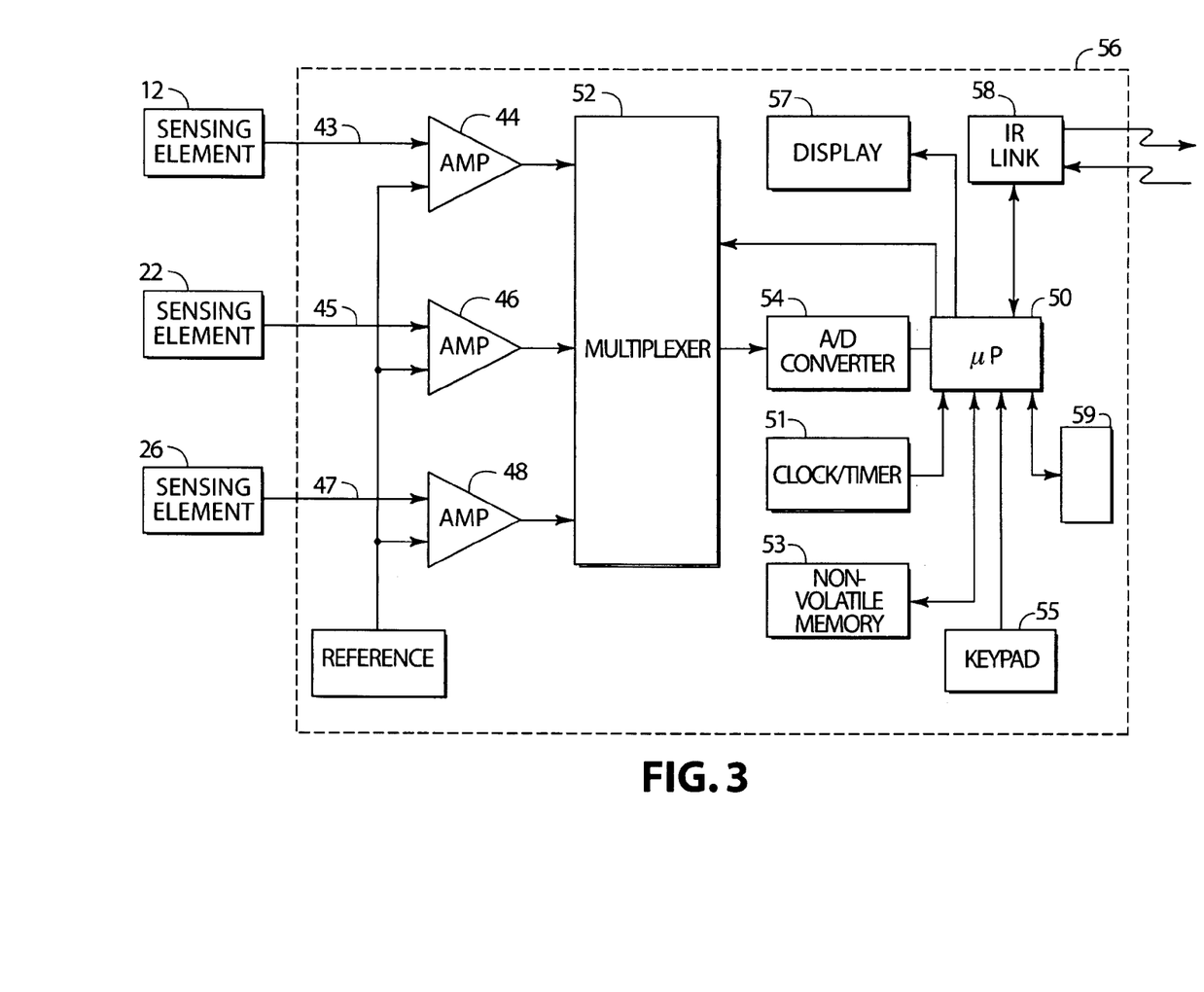
FIG. 3 is a function block diagram of a control circuit embodiment of the present invention.

A pharyngoesophageal monitoring system 10 according to this invention is illustrated in FIG. 1 positioned in a patient's pharyngoesophageal passage (P) for monitoring reflux of gastric acid from the stomach (S) into the esophagus (E) and pharynx (PH). The embodiment illustrated in FIGS. 1–3 shows a monitoring system 10 comprising a catheter (11) and having three sensors; however, probes having 1, 2, or even 4 or more pH sensors can be provided according to this invention. The monitoring system 10 comprises two probes 16, 28, each of which has one or more sensor arrangements 12, 22, 26, the sensor arrangements may each comprise one or a plurality of sensors and in some preferred embodiments pH sensors, and is attached at its proximal end 18, 30, respectively, to a connector 20. A sensor design may use the element Antimony (Sb, atomic number 51) as the pH sensing element, although other pH sensors can also be used. Monitoring systems in accordance with the present invention may also provide 3 or more probes. Each probe has wires (not illustrated) that carry voltages from the respective sensors 12, 22, 26, in preferred embodiments pH sensors, to the connector 20. The connector 20 connects or otherwise associates such wires in the probes 16, 28 to wires within the cord 21 to a recorder or data logger 56, which is preferably portable and can be worn in a shirt pocket or affixed to an article of clothing for ambulatory patients. As will be described in more detail below, pH sensor 12 is configured at or near the distal end 14 of probe 16. Likewise, pH sensors 22 and 26 are configured relative to each other at or near the distal end 24 of catheter 28.

In embodiment 10, the pH sensor 12 may be positioned by the first probe 16 in the distal portion of the esophagus $E_D$, i.e., just above the LES. The two pH sensors 22, 26 on the second probe 28 are spaced linearly apart from each other on probe 28 to straddle, i.e., be positioned on opposing sides of the UES, e.g. opposing pharyngoesophageal portions. Accordingly, the pH sensor 22 is positioned in the proximal esophagus $E_p$, i.e., just below the UES, while the pH sensor 26 is positioned in the pharynx P just above the UES. Since the UES is typically not very long and does not vary much in length from person to person, the spacing 27 between the two pH sensors 22, 26 can be pre-set and built into the probe 28 structure. However, the length of esophagi, i.e., the distances between the UES and the LES, varies from person to person. Therefore, the pH sensor 12 is positioned on separate probe 16, so it can be positioned upwardly or downwardly in relation to the pH sensor 22. In other words, the distance 23 between the pH sensor 12 and the pH sensor 22 can be varied or adjusted by moving the probe 16 longitudinally in relation to probe 28 or vice versa. Such variation or adjustment can be done anytime, while the probes 16, 28 are either inside or outside the person's body. However, it is preferred and will be more usual for the distance 23 between the pH sensor 12 and the pH sensor 22 to be set to a desired amount by the physician, nurse, or other practitioner prior to insertion of the catheters 16, 28 into the patient based on a previous determination of how much distance there is between the UES and the LES. As the desired distance 23 is attained between pH sensors 12, 22 by moving the probes 16, 28 longitudinally in relation to each other, one or both of the probes 16, 28 may have an adjustment or slack portion 29 that bulges or bows with respect to the other to accommodate the distance 23 selected. When the desired distance 23 is attained, the relative positions of the probes 16, 28, thus the distance 23 between the pH sensors 12, 22 is set or fixed by a suitable clamp 37, which is attached on the probes 16, 28 preferably, but not necessarily, far enough away from the sensors 12, 22 so as to be positioned outside the patient's body when the sensors 12, 22 are positioned at their desired locations in the distal esophagus $E_D$ and proximal esophagus $E_p$, respectively. A nose clamp 19 can be used to set and hold the probes 16, 28 in the desired positions in the patient's body to respectively position the sensors 12, 22, 26 in the desired positions in relation to the patient's LES and UES after the physician, nurse, or other practitioner has determined the distances between the patient's LES and UES, and nose. Graduation marks 13, 15, shown in FIG. 2, on probes 16, 28, respectively, such as in centimeter (cm) units, can facilitate the setting procedures described above.

It is preferred, but not essential, that the pH sensor 22 be positioned a short distance 31 from the distal end 24 of probe 28 to provide a stabilizer element or section 25, as best seen in FIG. 2. When the probe 28 is positioned in the patient's body, as illustrated in FIG. 1, the stabilizer section 25 extends farther into the patient's esophagus E than the pH sensor 22, which helps hold the position of pH sensor 22 within the esophagus during and after the patient's swallowing, and in some embodiments, in relation to the UES.

The pH sensor 22 is preferably, but not necessarily, located at a distance 31 of about five (5) centimeters from distal end 24 of probe 28, and the pH sensor 26 is preferably, but not necessarily, located at a distance 33 of about seven (7) cm proximally from sensor 22. Because the pH sensors 12, 22, 26 are attached to two probes 16, 28, sensors 22 and 26 can be adjusted longitudinally relative to sensor 12 along the pharyngoesophageal passage to place them in ideal locations for gathering data, e.g. data or signals regarding time, pH, and clearing time of gastroesophageal reflux episodes, as described above. As is shown in FIG. 1, when the patient has been properly intubated, sensor 12 will be located, preferably, but not necessarily, approximately 5 cm above the LES, thereby ensuring that sensor 12 is clear of the stomach S, and sensor 22 will be located, preferably, but not necessarily, approximately 5 cm below the patient's UES, and sensor 26 will be located, preferably, but not necessarily, approximately 2 cm above the UES, in the patient's pharynx (PH). In this configuration, the sensors 12, 22, 26 can accurately monitor changing pH levels at three locations along the patient's pharyngoesophageal passage and thereby determine when reflux episodes are occurring, the pH of the refluxate, the extent to which the refluxate moves into the distal esophagus $E_D$, the proximal esophagus $E_p$, and the pharynx (PH), as well as how long it takes to clear the refluxate from each of those portions of the pharyngoesophageal passage during each episode.

As described above, when located, the pH sensors 12, 22, 26 of monitoring probe apparatus 10 can provide an accurate picture of reflux activity in the patient's pharyngoesophageal passage. However, the information collected may be particularly useful if the data can be accurately plotted on a time line, showing at what time reflux episodes occur in relation to significant activities of the patient or group, such as eating, lying down, sleeping, or belching. If the patient is required to manually track when these significant events occur, such as in a diary, and then attempt to connect that information to the reflux activity data, the margin of error may be significant and unacceptable. If multiple recorders are used, each recorder logging data or signals received from a single pH sensor, the streams of data must then be spliced together to enable accurate analysis of the data versus elapsed time of the monitoring procedure. Again, a certain margin of error may be introduced to the data. As will be described below, the monitoring system 10 of the present invention overcomes these problems by using a single recorder responsive to data or signals, and in some embodiments integratively responsive to multiple sensors, so that pH data or signals from multiple sensors and event markers, are correlated, e.g. synchronized and integrated, with a common time clock in a common monitoring circuit before being stored in the microprocessor. As a result, the pH data and event markers can be accurately plotted versus elapsed time, with a negligible margin of error.

In accordance with one embodiment of the present invention, the monitoring system 10 may be connected via modular connector 20 to a recorder or data logger 56, as shown in FIG. 3. Sensors 12, 22, 26 transmit their respective signals to corresponding amplifiers 44, 46, 48, where the signals may be processed, in analog or digital fashion, and in the presently described embodiment, are amplified and conditioned before being routed to multiplexer 52. Multiplexer 52 then synchronizes transmission of the amplified signals received from the individual pH sensors 12, 22, 26, at predetermined data sample rates to an analog-to-digital (A/D) converter 54, which converts the signals from analog to digital format, and the digital signals are then received by the microprocessor 50 for correlation with timing and user inputs for storage, displays, and transmission to a computer for more detailed data processing, report generating, and long term storage. The microprocessor 50 receives timing and real time (year/month/day/hour/minutes/seconds) signals from a timer circuit 51 and its program from a non-volatile memory 53. It can also receive data input from a user input or keypad 55 or other input device, such device providing input such as the occurrence of pain, eating, lying down, sleeping, belching, and the like, which the microprocessor 50 correlates with time and pH sensor signals from the sensors 12, 22, 26. Such data can be stored in limited quantities for a short time in the microprocessor itself, or additional memory (not shown) can be provided. User control signals are also sent by the keypad 55 to the microprocessor 50. The microprocessor 50 outputs timing or multiplexing clock signals to the multiplexer 52 according to its programming. The microprocessor 50 also sends data signals to a display device (57), which can be a visual display, such as an LED display, sound generator, printer, or any combination of these or other display devices. Another function of the microprocessor 50 is to transmit data to a larger computer processing and storage facility (not shown) via any conventional link, such as an infrared (IR) communications link 58, hard wire interface 59, and the like.

Control, initiation, test, and other signals can also be transmitted to the microprocessor 50 from outside via the IR link 58 and/or interface 59.

Figure 4:
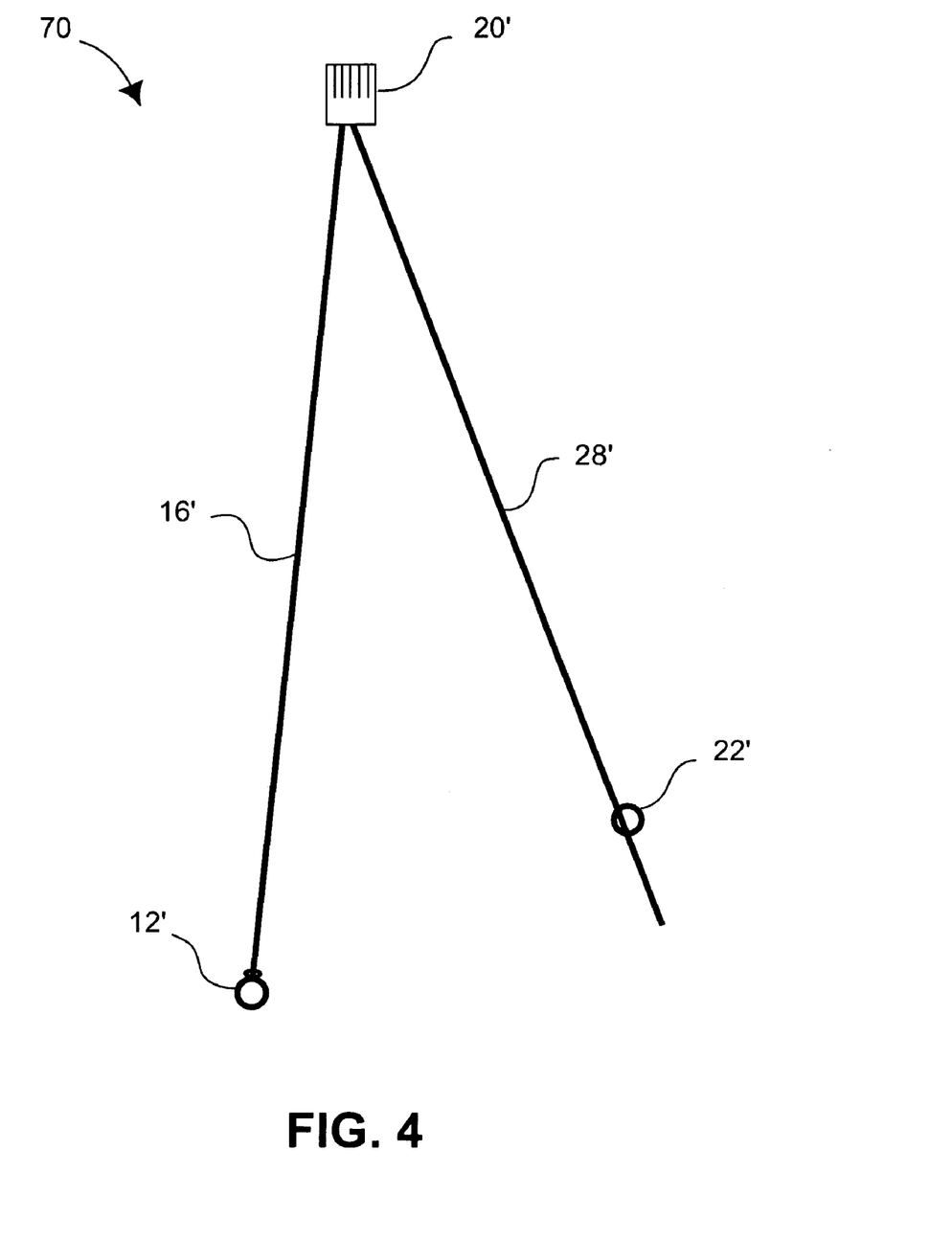
FIG. 4 is a diagrammatic view of an embodiment of the present invention having two sensors.
Figure 5A:
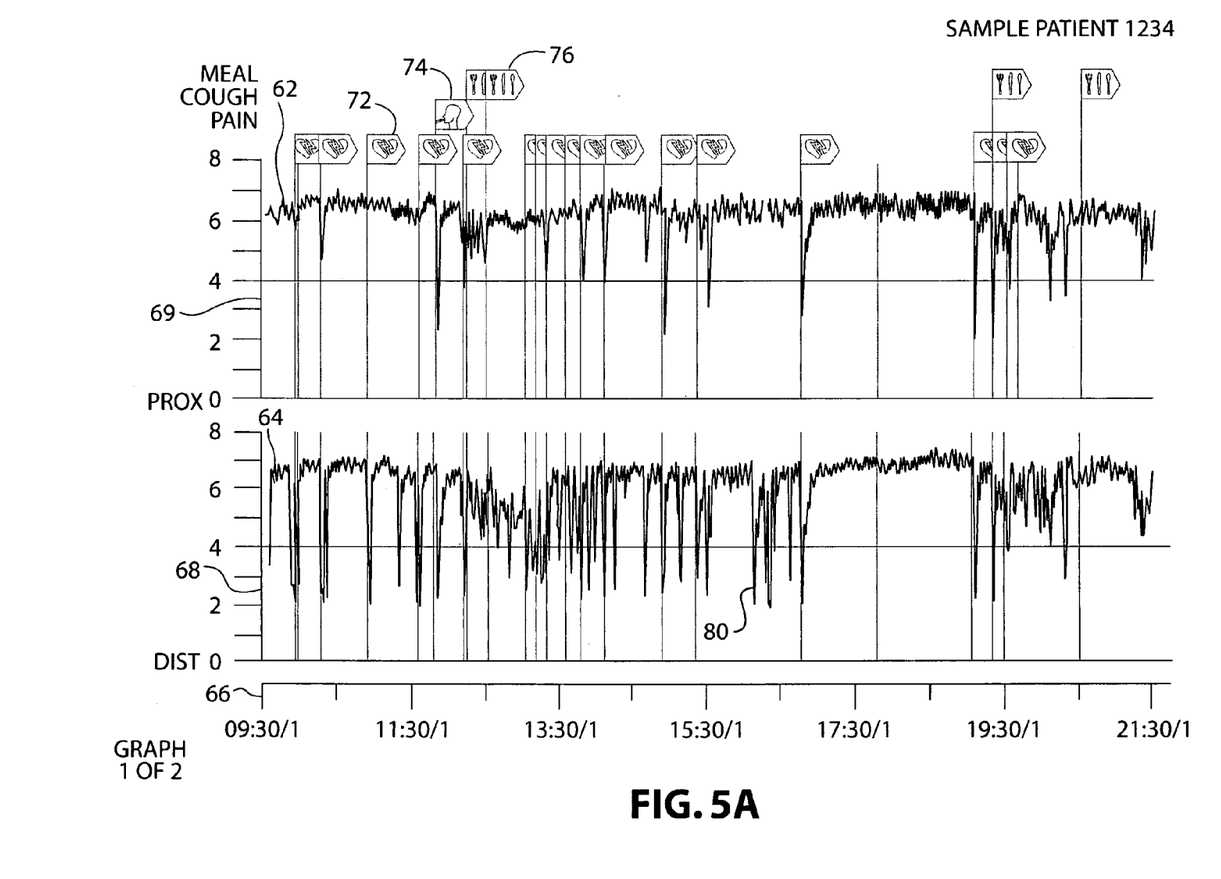
FIGS. 5A and 5B together are an exemplary patient graph plotting pH levels over time, recorded by the embodiment shown in FIG. 4, one sensor located proximally to the upper esophageal sphincter, and the other located distally to the UES, along with entered data marking episodes of heartburn, belching, and meals.
Figure 5B:
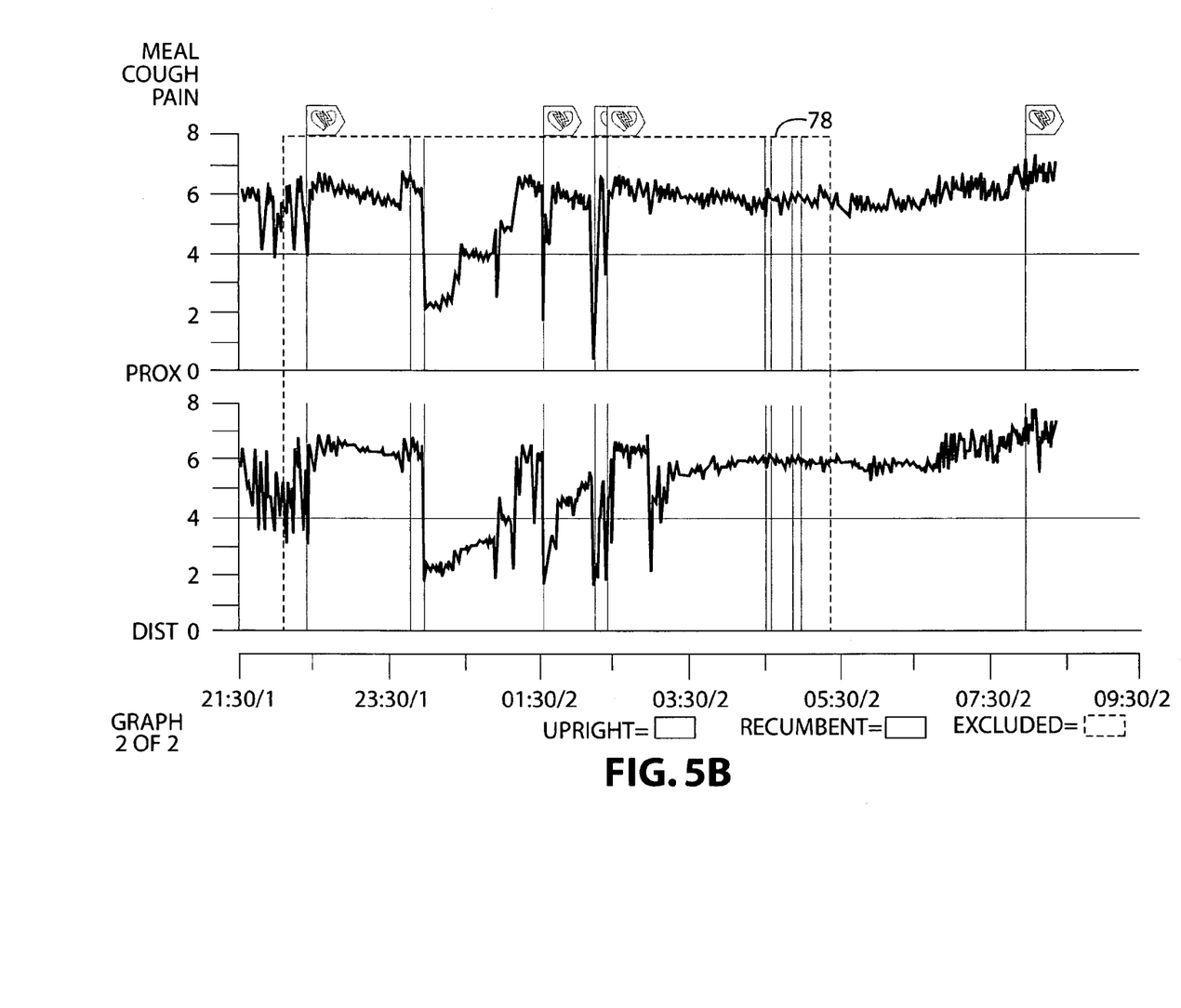

The transmitted data can subsequently be manipulated by a computer (not shown) to create graphs, charts, etc., or perform calculations to obtain various information that is desired by the physician overseeing the subject patient. FIGS. 5A–5B show a graph of the data obtained from a sample patient "1234" over a continuous 24-hour period, using pH probe apparatus 70, shown in FIG. 4, which uses two sensors, rather than three sensors shown in the monitoring system 10. However, the principles are the same. The data transmitted by sensor 22' is illustrated graphically by line 62, while data transmitted by distal sensor 12' is illustrated graphically by line 64. A common time clock 66 is shown along the x-axis, while the y-axes 68, 69 cover pH levels ranging from 0 (highly acidic) to 8 (slightly basic). Along the top margin of the combined graph are shown event markers indicating pain 72, cough 74, and a meal 76, while shaded region 78 in FIG. 5b indicates the patient is in a recumbent position. Each event marker is manually input into the recorder 56, e.g. via keypad 55, by the subject patient at the time the specific event occurred. For instance, point 80 on line 64 shows a pH reading approximately equal to 2.0. Since a pH level of 4.0 is considered normal for the region of the esophagus where the distal sensor is located, and the timing does not coincide with a "meal" event flag, this point 80 indicates a reflux episode occurring in the lower esophagus at about 10:55 a.m. Since there is not a corresponding drop in the proximal sensor graph line 62, the refluxate was limited to the distal esophagus and did not reach the proximal esophagus of the sample patient.

Figure 6:
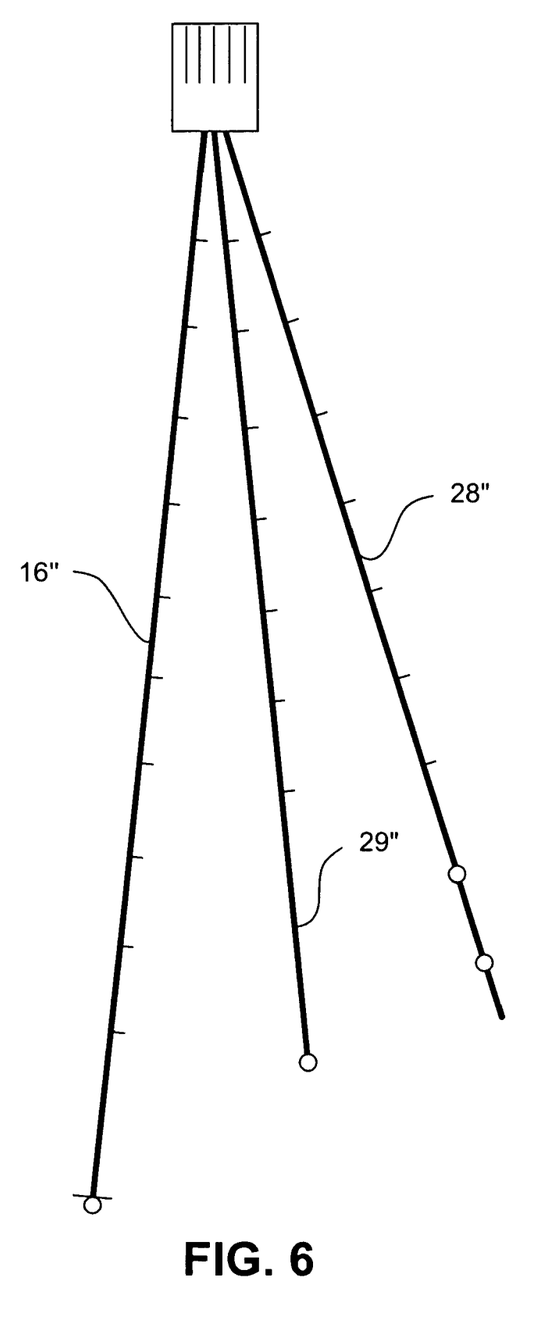
FIG. 6 is a diagrammatic view of an embodiment of the present invention having a third probe in addition to the first and second probes.

Another embodiment illustrated in FIG. 6 has three adjustable probes 16", 28", and 29" positioned adjacent each other. The sensors and scales on these thee probes 16", 28", and 29" are much the same as those described above.

Since numerous modifications and combinations of the above method and embodiments will readily occur to those skilled in the art, it is not desired to limit the invention to the exact construction and process shown and described above. Accordingly, resort may be made to all suitable modifications and equivalents that fall within the scope of the invention as defined by the claims which follow. The words "comprise," "comprises," "comprising," "include," "including," and "includes" when used in this specification and in the following claims are intended to specify the presence of stated features or steps, but they do not preclude the presence or addition of one or more other features, steps, or groups thereof.

We claim:

1. A pharyngoesophageal monitoring system, comprising:
   a. a first probe;
   b. a second probe adjacent said first probe;
   c. a first sensor arrangement configured at a position along said first probe;
   d. a second sensor arrangement configured at a position along said second probe;
   e. a slack portion in at least one of said probes and an adjustment element to which said probes are adjustably configurable; and
   f. a recorder responsive to said sensor arrangements;
   wherein said recorder is capable of correlation of signals generated by said sensor arrangements.

2. A pharyngoesophageal monitoring system as described in claim 1 wherein said first and second probes extend separately from a common connection.

3. A pharyngoesophageal monitoring system as described in claim 1 further comprising a third sensor arrangement configured at a position along said second probe.

4. A pharyngoesophageal monitoring system as described in claim 3 wherein said third sensor arrangement comprises at least one pH sensor.

5. A pharyngoesophageal monitoring system as described in claim 3 wherein said second sensor arrangement is configured at a position relative to said third sensor arrangement that accommodates positioning of said second sensor and said third sensor in opposing pharyngoesophageal portions proximate an upper esophageal sphincter of an individual.

6. A pharyngoesophageal monitoring system as described in claim 5 wherein said first sensor arrangement is adjustably configured to be locatable at a position corresponding to an esophageal portion of an individual.

7. A pharyngoesophageal monitoring system as described in claim 6 wherein first sensor arrangement is adjustably configured to be locatable at a position corresponding to a position proximate a lower esophageal sphincter of an individual.

8. A pharyngoesophageal monitoring system as described in claim 7 wherein said first probe is adjustably configurable in a manner that enables said first sensor to be set at a position approximately 5 centimeters above a lower esophageal sphincter of an individual.

9. A pharyngoesophageal monitoring system as described in claim 7 wherein said first sensor arrangement is configured at a position of about 5 centimeters from a distal end of said first probe.

10. A pharyngoesophageal monitoring system as described in claim 5 wherein said second sensor arrangement is configured at a distance of about 7 centimeters from said third sensor arrangement.

11. A pharyngoesophageal monitoring system as described in claim 1 or 5 wherein said first and said second sensor arrangements are adjustably configured at positions corresponding to an esophageal portion of an individual.

12. A pharyngoesophageal monitoring system as described in claim 1 or 5 wherein said first and said second sensor arrangements are adjustably configured at positions corresponding to an pharyngoesophageal portion of an individual.

13. A pharyngoesophageal monitoring system as described in claim 1 wherein said first sensor arrangement is configured at a substantially distal end of said first probe.

14. A pharyngoesophageal monitoring system as described in claim 1 or 13 wherein said second sensor arrangement is configured at a substantially distal end of said second probe.

15. A pharyngoesophageal monitoring system as described in claim 1 wherein at least one probe comprises a stabilizer element.

16. A pharyngoesophageal monitoring system as described in claim 15 wherein said stabilizer element comprises a stabilizer section configured at a distal end of said at least one probe.

17. A pharyngoesophageal monitoring system as described in claim 1 wherein at least one probe is adjustably configurable to enable setting the sensor arrangement on said at least one probe at a desired position in spatial relation to a upper esophageal sphincter of an individual.

18. A pharyngoesophageal monitoring system as described in claim 1 wherein at least one probe is adjustably configurable to enable setting the sensor arrangement on said at least one probe at a desired position in spatial relation to a lower esophageal sphincter of an individual.

19. A pharyngoesophageal monitoring system as described in claim 1 wherein one of said first and second probes is adjustably configurable to enable setting the sensor arrangement on said one of said first and second probes at a desired position in spatial relation to a upper esophageal sphincter of an individual and the other probe is adjustably configurable to enable setting the sensor arrangement on said other probe at a desired position in relation to a lower esophageal sphincter of an individual.

20. A pharyngoesophageal monitoring system as described in claim 1 wherein said adjustment element comprises a clamp.

21. A pharyngoesophageal monitoring system, comprising:
   a. a first probe;
   b. a second probe adjacent said first probe;
   c. a first sensor arrangement configured at a position along said first probe;
   d. a second sensor arrangement configured at a position along said second probe; and
   e. a recorder responsive to said sensor arrangements;
      wherein said recorder is capable of correlating signals generated by said sensor arrangements; and wherein at least one of said probes comprises a slack portion that accommodates spatial adjustment of the first and second sensor arrangements in relation to each other.

22. A method of pharyngoesophageal monitoring, comprising:
   a. inserting a first probe having a first sensor arrangement at least partially within at least a first portion of a pharyngoesophageal passage;
   b. inserting a second probe having a second sensor arrangement at least partially within at least a second portion of a pharyngoesophageal passage;
   c. adjustably configuring at least one of the probes corresponding to a selected part of an esophagus of an individual by taking up slack of at least a portion of at least one of the probes;
   d. sensing at least one characteristic of said first portion;
   e. generating at least one signal representative of said at least one characteristic of said first portion;
   f. sensing at least one characteristic of said second portion;
   g. generating at least one signal representative of said at least one characteristic of said second portion;
   h. receiving said signals representative of said characteristics of said first and second portions at a recorder;
   i. correlating said received signals representative of said characteristics with said recorder; and
   j. monitoring a correlation of received signals representative of said characteristics.

23. A method of pharyngoesophageal monitoring as described in claim 22 further comprising sensing at least one characteristic of at least a third portion of a pharyngoesophageal passage with a third sensor arrangement at least partially within said at least third portion.

24. A method of pharyngoesophageal monitoring as described in claim 22 wherein said receiving said signals comprises integratively receiving said signals representative of said characteristics of said first and second portions at said recorder.

25. A method of pharyngoesophageal monitoring as described in claims 22 or 23 wherein said sensing comprises sensing at least one pH of said respective portions.

26. A method of pharyngoesophageal monitoring as described in claim 25 further comprising receiving at least one signal selected from the group consisting of a time signal, a clearing time signal of a gastroesophageal reflux episode, and a user input signal.

27. A method of pharyngoesophageal monitoring as described in claim 26 wherein said user input signal comprises at least one event marker, said at least one event marker selected from the group consisting of a heartburn marker, a pain marker, an eating marker, a lying down marker, a sleeping marker, and a belching marker.

28. A method of pharyngoesophageal monitoring as described in claim 26 wherein said correlating said received signals comprises correlating said signals representative of said characteristics and said at least one signal selected from the group consisting of a time signal, a clearing time signal of a gastroesophageal reflux episode, and a user input signal.

29. An ambulatory record of data representative of gastroesophageal refluxate produced by the method described in claim 28.

30. An ambulatory record of data representative of gastroesophageal refluxate disease produced by the method described in claim 28.

31. An ambulatory record of data representative of gastroesophageal refluxate produced by the method of described in claim 22.

32. A method of pharyngoesophageal monitoring as described in claim 22 or 23 further comprising receiving at least one signal selected from the group consisting of a time signal, a clearing time signal of a gastroesophageal reflux episode, and a user input signal.

33. A method of pharyngoesophageal monitoring as described in claim 32 wherein said user input signal comprises at least one event marker, said at least one event marker selected from the group consisting of a heartburn marker, a pain marker, an eating marker, a lying down marker, a sleeping marker, and a belching marker.

34. A method of pharyngoesophageal monitoring as described in claim 32 wherein said correlating said received signals comprises correlating said signals representative of said characteristics and said at least one signal selected from the group consisting of a time signal, a clearing time signal of a gastroesophageal reflux episode, and a user input signal.

35. An ambulatory record of data representative of gastroesophageal refluxate produced by the method described in claim 34.

36. An ambulatory record of data representative of gastroesophageal refluxate disease produced by the method described in claim 34.

37. An ambulatory record of data representative of gastroesophageal refluxate disease produced by the method described in claim 22.

38. A method of pharyngoesophageal monitoring as described in claim 22 wherein said inserting said first and second probes are performed substantially simultaneously.

39. A method of pharyngoesophageal monitoring as described in claim 22 wherein said inserting a second probe comprises inserting a second probe having a second sensor arrangement at least partially within at least a third portion of a pharyngoesophageal passage and further comprising:
   a. sensing at least one characteristic of said third portion;
   b. generating at least one signal representative of said at least one characteristic of said third portion; and
   c. receiving said signals representative of said characteristics of said first, second and third portions at said recorder.

40. A method of pharyngoesophageal monitoring as described in claim 22 wherein said inserting a second probe having a second sensor arrangement at least partially within at least a second portion of a pharyngoesophageal passage comprises inserting said second probe such that said second sensor arrangement is positioned proximate a upper esophageal sphincter of an individual.

41. A method of pharyngoesophageal monitoring as described in claim 40 wherein said second portion corresponds to a pharyngoesophageal portion proximate a upper esophageal sphincter of an individual.

42. A method of pharyngoesophageal monitoring as described in claim 40 wherein said inserting a second probe comprises inserting a second probe having a third sensor arrangement at least partially within at least a third portion of a pharyngoesophageal passage and further comprising:
  a. sensing at least one characteristic of said third portion;
  b. generating at least one signal representative of said at least one characteristic of said third portion; and
  c. receiving said signals representative of said characteristics of said first, second and third portions at said recorder.

43. A method of pharyngoesophageal monitoring as described in claim 42 wherein said second and third portions correspond to opposing pharyngoesophageal portions proximate a upper esophageal sphincter of an individual.

44. A method of pharyngoesophageal monitoring as described in claim 39 or 43 further comprising the step of configuring said second sensor arrangement a distance of about 7 centimeters from said third sensor arrangement.

45. A method of pharyngoesophageal monitoring as described in claim 44 wherein said first portion corresponds to a pharyngoesophageal portion proximate a lower esophageal sphincter of an individual.

46. A method of pharyngoesophageal monitoring as described in claim 22, 40 or 43 wherein said inserting a first probe having a first sensor arrangement at least partially within at least a first portion of a pharyngoesophageal passage comprises inserting said first probe such that said first sensor arrangement is positioned proximate a lower esophageal sphincter of an individual.

47. A method of pharyngoesophageal monitoring as described in claim 46 wherein said inserting said first probe such that said first sensor arrangement is positioned proximate a lower esophageal sphincter of an individual comprises positioning said first sensor arrangement about 5 centimeters above the lower esophageal sphincter.

48. A method of pharyngoesophageal monitoring as described in claim 22 further comprising stabilizing at least one probe within a pharyngoesophageal passage.

49. A method of pharyngoesophageal monitoring as described in claim 48 wherein said stabilizing is provided at a distal end of said at least one probe.

50. A method of pharyngoesophageal monitoring as described in claim 22 or 24 further comprising adjustably configuring at least one probe corresponding to a upper esophageal sphincter of an individual.

51. A method of pharyngoesophageal monitoring as described in claim 22 or 24 further comprising adjustably configuring at least one probe corresponding to a lower esophageal sphincter of an individual.

52. A method of pharyngoesophageal monitoring, comprising:
  a. inserting a first probe having a first sensor arrangement at least partially within at least a first portion of a pharyngoesophageal passage;
  b. inserting a second probe having a second sensor arrangement at least partially within at least a second portion of a pharyngoesophageal passage;
  c. adjustably configuring at least one of the probes corresponding to a selected part of an esophagus of an individual by taking up slack of at least a portion of at least one probe;
  d. sensing at least one characteristic of said first portion;
  e. generating at least one signal representative of said at least one characteristic of said first portion;
  f. sensing at least one characteristic of said second portion;
  g. generating at least one signal representative of said at least one characteristic of said second portion;
  h. receiving said signals representative of said characteristics of said first and second portions at a recorder;
  i. correlating said received signals representative of said characteristics with said recorder; and
  j. monitoring a correlation of received signals representative of said characteristics.

* * * * *